United States Patent [19]

Lowder

[11] Patent Number: 4,645,497
[45] Date of Patent: Feb. 24, 1987

[54] COLONIC IRRIGATION BOARD

[76] Inventor: Eldon L. Lowder, 7835 South 1300 E., Sandy, Utah 84092

[21] Appl. No.: 812,187

[22] Filed: Dec. 23, 1985

Related U.S. Application Data

[63] Continuation of Ser. No. 566,034, Dec. 27, 1983, abandoned.

[51] Int. Cl.$^4$ ............................................. A61M 31/00
[52] U.S. Cl. ..................................... 604/276; 604/356
[58] Field of Search ............... 604/275, 276, 277, 279, 604/322, 326, 327, 356, 357; 4/443–448

[56] References Cited

U.S. PATENT DOCUMENTS

| | | | |
|---|---|---|---|
| 1,822,206 | 9/1931 | Ferguson | 604/322 |
| 2,176,235 | 10/1939 | Woodward | 604/322 |
| 2,818,862 | 1/1958 | Wanek | 604/276 |
| 2,852,025 | 9/1958 | Wessels | 604/276 |
| 3,416,529 | 12/1968 | Weisman | 604/276 |
| 4,221,371 | 9/1980 | Kuphal | 604/356 |
| 4,321,920 | 3/1982 | Gillig | 604/275 |

FOREIGN PATENT DOCUMENTS 594746  3/1934  Fed. Rep. of Germany ...... 604/275

Primary Examiner—Dalton L. Truluck
Assistant Examiner—Mario Costantino
Attorney, Agent, or Firm—Thorpe, North & Western

[57] ABSTRACT

A one piece colonic irrigation board having a generally elongate support table with a width and length which allows a person to lie comfortably thereon. The table includes an opening at a rear end thereof and a catch basin formed over the opening for receiving and directing downwardly fecal matter. The catch basin includes side walls disposed on each side of the opening, and a rear/top wall disposed at the rear of the opening to slope upwardly and forwardly over the opening, with the forward edges of the side walls and the rear/top wall defining a generally vertically oriented opening whose lower edge is adjacent to the forward edge of the opening in the table. A tube extends through the rear/top wall of the catch basin and out the generally vertical opening to deliver liquid to the colon of the person lying on the table. The upper surface of the table in front of the opening is formed to slope downwardly and inwardly from the sides and rearwardly into the opening. A lip is formed to project upwardly from the side edges of the board to retain fecal matter and prevent it from running off the edge of the board.

6 Claims, 2 Drawing Figures

COLONIC IRRIGATION BOARD

This application is a continuation of application Ser. No. 566,034, filed Dec. 27, 1983 abandoned.

BACKGROUND OF THE INVENTION

This invention relates to a colonic irrigation board which is simple to use and easy to clean and maintain.

Colonic boards have been used for some time as a means for self-administering enemas. In addition to the traditional health benefits of enemas, users of colonic boards often times find that periodic colonic irrigations serve to improve general well being and health.

Conventional colonic boards typically consist of an elongate, flat and narrow (about 15 inches in width) boards having and opening at one end over which is fitted a box-like catch basin. A fairly rigid proctal extends through the back of the catch basin from the opening in the front thereof and is connected to an elevated source of water. A person using the colonic board simply lies on the board so that the proctal is inserted into the rectum, and then the water is allowed to flow through the proctal at a rate controlled by the user. Conventional colonic boards, however, are relatively uncomfortable because of the generally flat upper surface and the narrowness thereof. Also, the construction and shape of the catch basin can easily result in fecal matter splashing back onto the board surface and, since the upper surface of the board is generally flat, the fecal matter may flow over the edge of the board.

SUMMARY OF THE INVENTION

It is an object of the invention to provide a colonic irrigation board which is simple in design and yet sturdy in construction.

It is another object of the invention to provide such a colonic irrigation board which may be readily utilized with any toilet.

It is a further object of the invention to provide a colonic irrigation board which is designed to prevent splashing of fecal matter back onto the surface of the board and to guide any fecal matter back into the catch basin and into a toilet or container on which the board is placed.

The above and other objects of the invention are realized in a specific illustrative embodiment thereof which includes an elongate support table having a width and length which enables a person to lie comfortably thereon, with the table having an opening at a rear end thereof. Also included is a catch basin formed at the rear end of the table over the opening for receiving and directing downwardly fecal matter. The catch basin includes side walls disposed on each side of the opening, and a rear/top wall disposed at the rear of the opening to slope upwardly and forwardly over the opening, with the forward edges of the side walls and the rear/top wall defining a generally vertically oriented opening whose lower edge is adjacent to the forward edge of the opening in the table. A tube extends through the rear/top wall of the catch basin and extends through the generally vertical opening to deliver liquid to the colon of a person lying on the table.

In accordance with one aspect of the invention, the upper surface of the table in front of the openings is formed to slope downwardly and inwardly from the sides and rearwardly into the openings. Also, a lip is formed to project upwardly from the side edges of the board to retain fecal matter and prevent it from running off the edge of the board.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
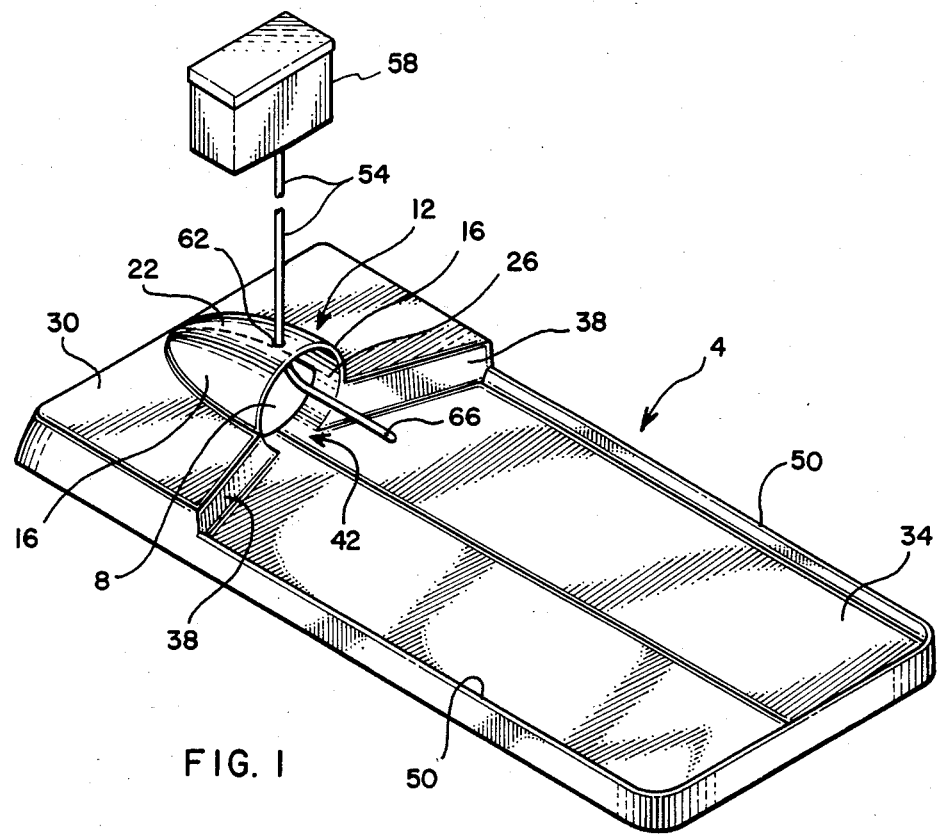
FIG. 1 shows a perspective view of a colonic irrigation board made in accordance with the principles of the present invention.

Referring to the drawings, there is shown a specific illustrative embodiment of a colonic irrigation board which includes an elongate support table having a width of about 20 inches or greater, with the preferred width being about 24 inches. An opening 8 is formed at the rear end of the board. Formed over the opening 8 is a so-called catch basin 12.

The catch basin 12 includes side walls 16 which project upwardly from the lateral edges of the opening 8, and a rear/top wall 22 which extends upwardly and forwardly from the rear edge of the opening 8. The forward edges of the side walls 16 and rear/top wall 22 join to define a generally vertically oriented opening 26 in the catch basin 12. The lower edge of the opening 26 is adjacent or contiguous to the forward edge of the opening 8 as best seen in FIG. 1. The sloping rear/top wall 22 serves to direct downwardly fecal matter which is discharged by a person lying on the table 4 into the catch basin 12.

Figure 2:
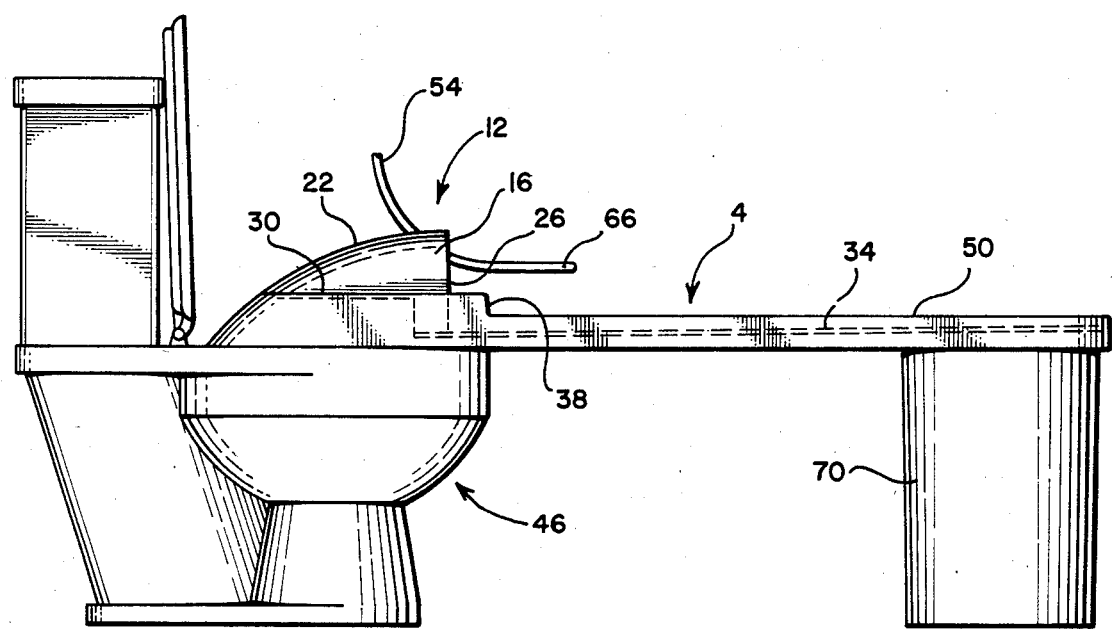
FIG. 2 shows a side, elevational view of the colonic irrigation board of FIG. 1 as it might be mounted on a toilet and bucket.

The upper surface of the table 4 is composed of an upper level 30 and a lower level 34 joined by a ledge 38. The upper level 30 surrounds the catch basin 12 while the lower level 34 is for lying on by a person using the colonic board. The upper surface of the lower level 34 is formed to slope downwardly and inwardly from the sides, and rearwardly toward the openings 8 and 26, as best seen in FIG. 1. With this upper surface configuration, fecal matter, liquid, etc. will be drawn by gravity toward the openings 26 and 8. A spillway 42 is formed immediately in front of the openings 26 and 8 so that fecal matter and liquid will flow from the lower level 34 into the openings 26 and 8 and then downwardly into a container or toilet 46 as shown in FIG. 2.

An upwardly projecting lip 50 is formed on the edge of the lower level 34 of the colonic board to retain liquid and material on the upper surface of the board and prevent such liquid and material from flowing over the edges of the board. The lip extends from a ledge 38 forwardly to circumscribe the lower level 34 of the colonic board.

Advantageously, the colonic board 4 is formed of one piece of material such as fiberglass to provide a seamless, single piece board. The precise dimensions of the board can be elected to suit the typical user, but it has been found advantageous to provide a board of between 42 inches and 48 inches in length and, as indicated earlier, 22 inches in width.

A flexible tube 54 extends from an elevated source of liquid 58 through an opening 62 in the rear/top wall of the catch basin 12 and out the opening 26 as shown. The free end of the tube 54, typically referred to as a proctal, is positioned to enable ready insertion into the rectum of a person lying on the colonic board 4. The tip of the free end of the tube 54 is closed, and an opening 66 is formed in the side wall of the tube a short distance from the tip. Placement of the opening 66 on the side of the tube, rather than the end, reduces the liklihood of the opening becoming clogged when used.

The tube 54 could be made of a variety of flexible materials including rubber and plastic.

FIG. 2 shows the colonic board 4 placed on a conventional toilet 46 and bucket 70 or other support. The board 4 is positioned so that the opening 8 is directly over the toilet bowl so that fecal matter discharged by a person using the board will be directed downwardly by the catch basin 12 into the toilet.

The colonic board discribed is sturdy in construction and convenient to use. The dimensions of the board allow a person to lie comfortably thereon. The design of the catch basin 12 and provision of the sloping upper surface 34 and upstanding lip 50 serve to eliminate splashing and spilling of fecal matter and liquid.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A colonic board comprising
   an elongate support table having a width and length which enables a person to lie thereon, said table having an opening at a rear end thereof, the upper surface of the table in front of the opening being formed to slope downwardly and inwardly from the sides, and rearwardly into the opening, said table including an upwardly projecting lip formed at the edges of the table forwardly of the catch basin, to circumscribe the upper surface of the table,
   a catch basin formed integrally with the support table at said rear end of the table over the opening for receiving and directing downwardly fecal matter, said catch basin including side walls disposed on each side of the opening, and a rear/top wall disposed at the rear of the opening and sloping substantially its entire length at an acute angle upwardly and forwardly over the opening so as to divert downwardly toward the opening fecal matter which may strike the wall, with the forward edges of side walls and rear/top wall defining a generally vertically oriented opening whose lower edge is adjacent the forward edge of the opening in the table, and
   tubular means for delivering liquid to the colon of a person lying on the table.

2. A colonic board as in claim 1 wherein the table and catch basin are made of fiberglass.

3. A colonic board as in claim 1 wherein the tubular means comprises a flexible tube, one end of which is for insertion in a person's rectum and the other end of which is for coupling to a source of liquid, and wherein the rear/top wall of the catch basin includes an opening through which said one end of the tube may be inserted.

4. A colonic board as in claim 3 wherein said tube is closed at said one end and includes an opening in the side of the tube near said one end.

5. A colonic board as in claim 1 wherein said table has a width of about twenty inches or greater.

6. A colonic board as in claim 5 wherein said table is about forty-two inches or greater in length.

* * * * *